(12) United States Patent
Baskin et al.

(10) Patent No.: US 7,267,945 B2
(45) Date of Patent: Sep. 11, 2007

(54) METHODS OF DETERMINING THE PRESENCE OF POLYNUCLEOTIDES EMPLOYING AMPLIFICATION

(75) Inventors: Dale Baskin, Cliffside Park, NJ (US); Robert Brankamp, West Chester, OH (US); Marcia Slater, Perkiomenville, PA (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 09/818,086

(22) Filed: Mar. 26, 2001

(65) Prior Publication Data

US 2002/0137047 A1    Sep. 26, 2002

(51) Int. Cl.
*C12Q 1/68*    (2006.01)
*C12P 19/34*    (2006.01)
*C07H 21/04*    (2006.01)
*C07H 21/00*    (2006.01)

(52) U.S. Cl. .................. 435/6; 435/91.2; 536/24.3; 536/25.32

(58) Field of Classification Search ............ 435/6, 435/91.2; 536/24.3, 25.32
See application file for complete search history.

(56) References Cited

U.S. PATENT DOCUMENTS

| | | | |
|---|---|---|---|
| 5,436,134 A | 7/1995 | Haugland et al. | 435/34 |
| 5,538,848 A | 7/1996 | Livak et al. | 435/5 |
| 5,563,037 A | 10/1996 | Sutherland et al. | 435/6 |
| 5,723,591 A | 3/1998 | Livak et al. | 536/22.1 |
| 5,928,907 A | 7/1999 | Woudenberg et al. | 435/91.2 |
| 6,015,674 A | 1/2000 | Woudenberg et al. | 435/6 |
| 6,103,465 A | 8/2000 | Johnston-Dow et al. | 435/6 |
| 6,154,707 A | 11/2000 | Livak et al. | 702/20 |
| 6,174,670 B1 | 1/2001 | Wittwer et al. | 435/6 |
| 6,790,945 B2 * | 9/2004 | Lukhtanov et al. | 536/23.1 |

FOREIGN PATENT DOCUMENTS

| | | |
|---|---|---|
| EP | 0 487 218 A1 | 5/1992 |
| WO | WO92/15711 | 9/1992 |

OTHER PUBLICATIONS

Pritham et al., "Continuous Flouresecent Monitoring of Rapid Cycle Polymerase Chain Reaction", Clinical Ligand Assay, vol. 21, No. 4, pp. 404-412 (1998).*
Wittwer et al., "Continuous Flourescence Monitoring of Rapid Cycle DNA Amplification," *BioTechniques*, 22:130-138 (1997).
International Search Report for PCT Application No. PCT/US02/03414, mailed Mar. 27, 2003.
Hnatyszyn, H. J. et al., 2001, "The Use of Real-Time PCR and Fluorogenic Probes for Rapid and Accurate Genotyping of Newborn Mice," Molecular and Cellular Probes, 15:169-175 (PubMed Abstract (showing date of "Jun. 2001") and Full-Text Article).

* cited by examiner

*Primary Examiner*—Kenneth R. Horlick
*Assistant Examiner*—Joyce Tung
(74) *Attorney, Agent, or Firm*—Finnegan, Henderson, Farabow, Garrett & Dunner, LLP.; Andrew K. Finn

(57) ABSTRACT

The invention provides methods and kits for determining the presence of polynucleotides in samples. According to certain embodiments, the invention provides methods for determining the presence of target polynucleotides by amplifying the target polynucleotides in the sample, detecting amplification products, and determining the sequence of the amplification products.

25 Claims, 4 Drawing Sheets
(4 of 4 Drawing Sheet(s) Filed in Color)

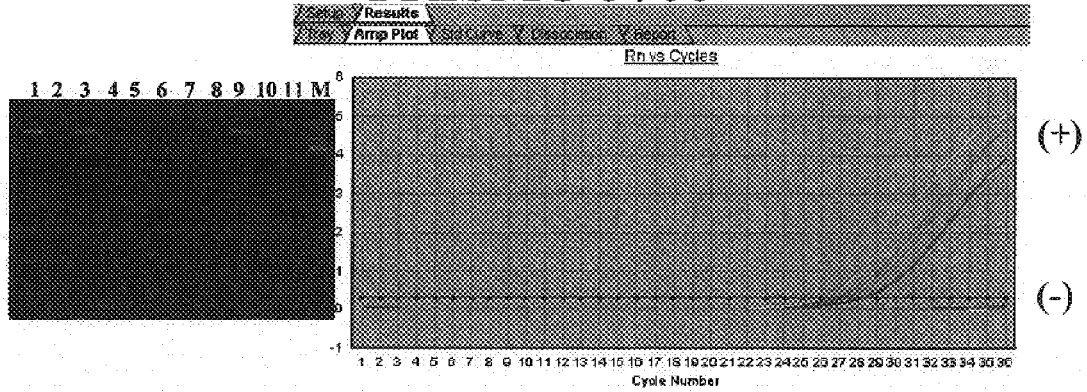

Figure 1. The agarose gel and the ABI PRISM® 5700 show different methods of evaluating PCR results. The gel shows the three positive PCR reactions (Lanes 1, 3 & 9), as well as a control ladder (Lane 12). The agarose gel also shows eight negative PCR reactions. The ABI PRISM® 5700 Sequence Detection System generates an Amplification Plot, which is a measurement of the increase in fluorescence of SYBR green. This increase correlates to an increase of PCR products. The above Amplification Plot shows the four positive reactions (+), and the eight negative reactions (-). The data in the Amplification Plot was collected during the PCR amplification, and the analyzed data was available immediately upon completion of the PCR reactions. The gel shows three positive reactions and not four because the positive control was not loaded, and the control ladder was run in its place.

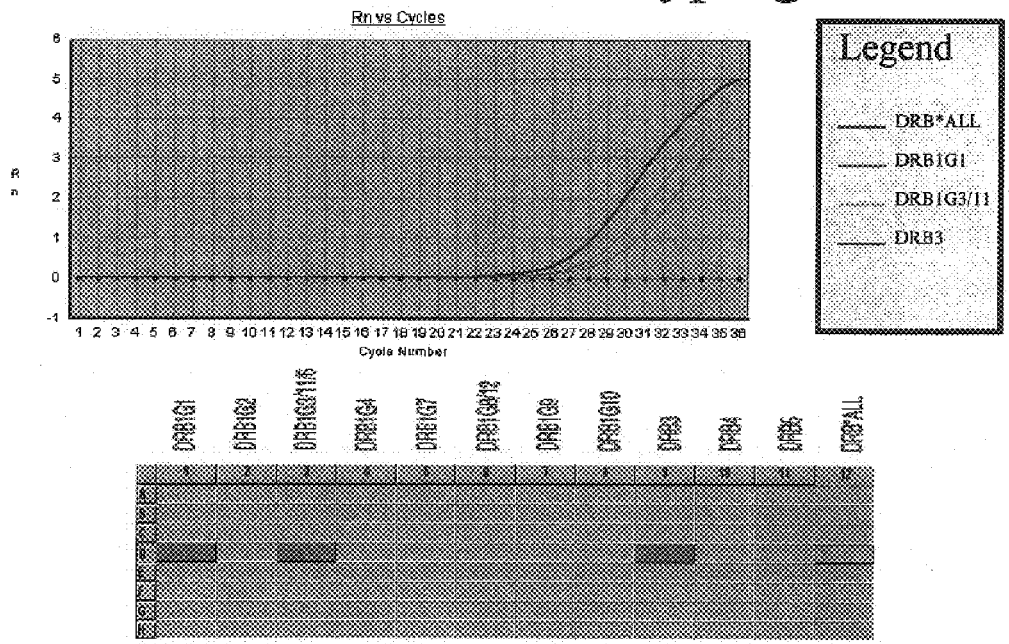
Figure 2. Based on the PCR results, this person is positive for DRB1G1, DRB1G3/11/6 and DRB3. This is an expected combination. This completes the low resolution typing of this individual. These same PCR products were then used for high resolution typing.

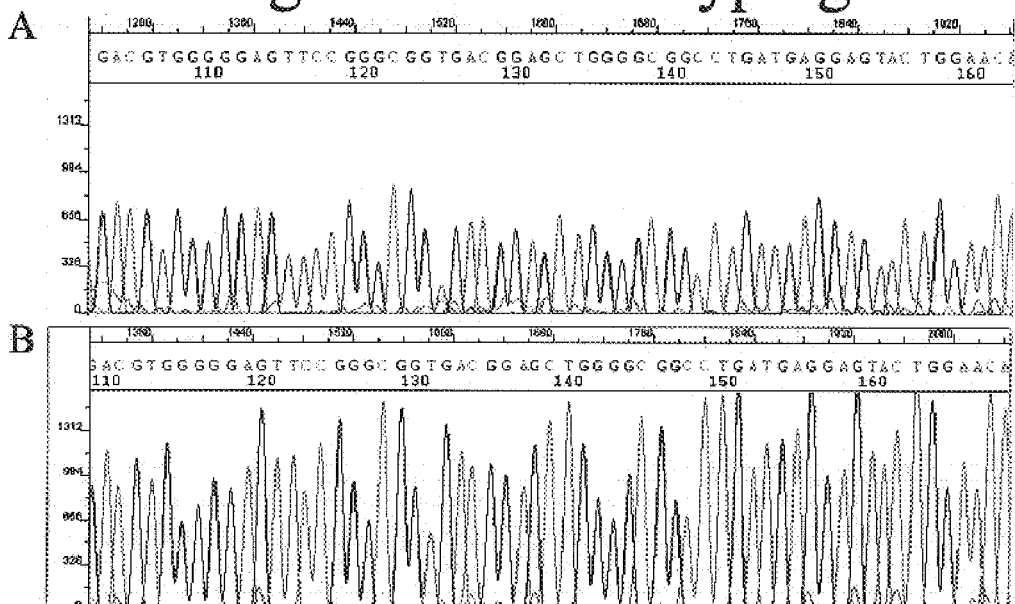

Figure 3. Panel A, shows sequence data from a PCR product produced using the standard HLA protocol. Panel B, shows sequence data from a PCR product generated using the modified SYBR/HLA protocol. Each sample was immediately sequenced after low resolution typing was completed. This comparison of data shows, the addition of SYBR® Green PCR Master Mix had no adverse effect on the sequencing reaction. This data was produced on the ABI PRISM® 3100 Genetic Analyzer.

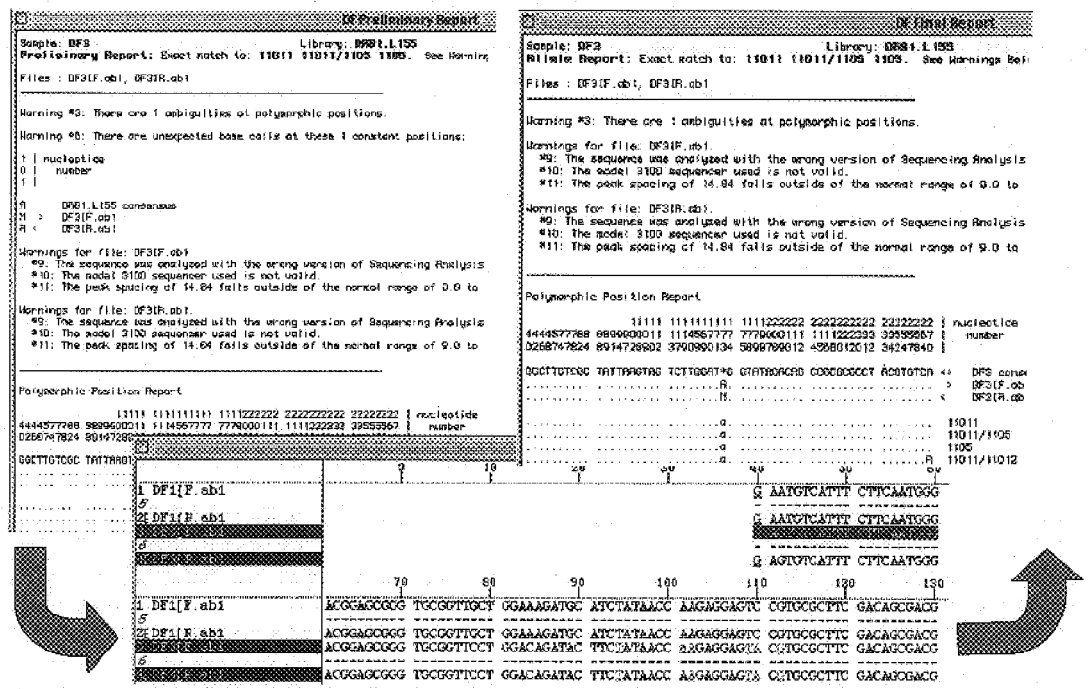

Figure 4. This panel shows the completion of the high resolution typing. The sequenced sample data was analyzed by the Applied Biosystems MatchTools™ software to get a Preliminary Report. The data was then edited in Applied Biosystems MT Navigator software, before being resubmitted to the Applied Biosystems MatchTools™ software for a Final Report. This sample was an exact match to 11011, 11011/1105, 1105.

METHODS OF DETERMINING THE PRESENCE OF POLYNUCLEOTIDES EMPLOYING AMPLIFICATION

FIELD OF THE INVENTION

The invention relates generally to the field of nucleic acid amplification, including detecting polynucleotide products from amplification reactions. The invention also relates to methods and kits for detecting nucleic acid sequences.

BACKGROUND OF THE INVENTION

Nucleic acid analysis is important in many research and medical diagnostic fields.

Often analysis of amplified nucleic acid involves running the amplified product on gels to determine whether particular products have been amplified. Amplified products, such as those obtained from PCR reactions, are typically loaded and electrophoretically resolved on agarose or polyacrylamide gels.

Analysis after electrophoresis typically involves staining the gel with a fluorescent dye, such as ethidium bromide, which intercalates with double stranded DNA. The gel is then subjectively analyzed by a human, who must guess at relative band intensities and distances against a background fluorescence in the non-DNA portion of the rest of the gel. Such subjective analysis is often subject to human error, and increases the time required for analysis as the technician records the results of each reaction manually.

SUMMARY OF THE INVENTION

According to certain embodiments of the invention, methods of determining the presence and sequence of at least one target polynucleotide in a sample are provided. Such methods comprise combining nucleic acid from the sample with at least one reaction composition comprising a fluorescent indicator and amplification primers specific to the at least one target polynucleotide. The method further comprises amplifying the at least one target polynucleotide present in the at least one reaction composition using the amplification primers to obtain at least one amplification product. The at least one amplification product is irradiated such that the fluorescent indicator produces a fluorescent signal, wherein the intensity of the signal is related to the quantity of amplification product. The method further comprises monitoring the amplifying by detecting the fluorescent signal from the fluorescent indicator, and determining whether the at least one amplification product is present. If the at least one amplification product is present in the reaction composition, one then determines the sequence of the at least one amplification product.

In certain embodiments of the invention, methods of determining the presence and sequence of at least one target polynucleotide in a sample comprise combining nucleic acid from the sample with at least one set of reaction compositions comprising a first reaction composition and a second reaction composition, both specific for the at least one target polynucleotide. The first reaction composition comprises amplification primers specific to the at least one target polynucleotide, and the second reaction composition comprises a fluorescent indicator and amplification primers specific to the at least one target polynucleotide. The method further comprises amplifying the at least one target polynucleotide present in the reaction compositions using the amplification primers to obtain at least one amplification product. The at least one amplification product of the second reaction composition is irradiated such that the fluorescent indicator produces a fluorescent signal, wherein the intensity of the signal is related to the quantity of the at least one amplification product. The method further comprises monitoring the amplifying of the second reaction composition by detecting the fluorescent signal from the fluorescent indicator, and determining whether the at least one amplification product is present in both the first reaction composition and second reaction composition from the intensity of signal from the fluorescent indicator in the second reaction composition. If the at least one amplification product is present in the first reaction composition, one then determines the sequence of the at least one amplification product from the amplification product of the first reaction composition.

In certain embodiments, nucleic acid from the sample is combined with at least two different separate reaction compositions, wherein each reaction composition comprises a fluorescent indicator and a different set of amplification primers specific to a different target polynucleotide. The amplifying results in different amplification products if the different target polynucleotides are present in the sample.

In certain embodiments, the presence of a given target polynucleotide indicates the presence of a specific allele. In certain embodiments, the presence of one or more alleles indicates one or more cell surface proteins which determine at least one HLA type. In certain embodiments, the at least one HLA type comprises at least one of, but is not limited to, HLA-A, HLA-B, HLA-C, HLA-E, HLA-F, HLA-G, HLA-DRA, HLA-DRB1, HLA-DRB2, HLA-DRB3, HLA-DRB4, HLA-DRB5, HLA-DQA1, HLA-DQB1, HLA-DPA1, HLA-DPB1, HLA-DOA, HLA-DOB, HLA-DMA, and HLA-DMB.

In certain embodiments, a kit for performing amplification and sequencing reactions on a sample is provided. According to certain embodiments, the kit comprises amplification primers designed for amplification of at least one target polynucleotide in a sample to obtain at least one amplification product, a fluorescent indicator whose intensity is related to the amount of amplification product generated in an amplification reaction, and sequencing primers specific to the at least one amplification product.

BRIEF DESCRIPTION OF THE FIGURES

The patent or application file contains at least one drawing executed in color. Copies of this patent or patent application publication with color drawings will be provided by the Office upon request and payment of the necessary fee.

FIG. 1 shows a comparison of the results of amplification reactions analyzed by agarose gel electrophoresis and by the ABI Prism® 5700, an apparatus which is capable of thermal cycling, emitting a beam of light, and detecting fluorescence in a reaction sample.

FIG. 2 shows the results of low resolution HLA-DRB typing using the ABI Prism® 5700.

FIG. 3 shows the results of high resolution HLA-DRB typing using an ABI Prism 3100 genetic analyzer.

FIG. 4 shows a complete analysis of high resolution HLA-DRB typing, showing which specific HLA-DRB alleles were present in the sample.

DETAILED DESCRIPTION OF THE INVENTION

All documents cited in this application, including but not limited to patents, patent applications, articles, books, and treatises, are expressly incorporated by reference in their entirety for any purpose.

Definitions

The terms "polynucleotide" and "oligonucleotide" mean polymers of nucleotide monomers, including analogs of such polymers, including double and single stranded deoxyribonucleotides, ribonucleotides, α-anomeric forms thereof, and the like. Descriptions of how to synthesize oligonucleotides can be found, among other places, in U.S. Pat. Nos. 4,373,071; 4,401,796; 4,415,732; 4,458,066; 4,500,707; 4,668,777; 4,973,679; 5,047,524; 5,132,418; 5,153,319; and 5,262,530. Polynucleotides and oligonucleotides can be of any length.

"Amplification primers" are oligonucleotides that comprise sequences that are employed in an amplification reaction to amplify specific target polynucleotides. Amplification primers according to the present invention refer to oligonucleotides that are designed to hybridize with a portion of the target polynucleotide or amplification products in a sequence-specific manner, and serve as primers for amplification reactions.

The criteria for designing sequence-specific primers are well known to persons of skill in the art. Detailed descriptions of primer design that provide for sequence-specific annealing can be found, among other places, in Diffenbach and Dveksler, PCR Primer, A Laboratory Manual, Cold Spring Harbor Press, 1995, and Kwok et al. (Nucl. Acid Res. 18:999-1005, 1990). The sequence-specific portions of the primers are of sufficient length to permit specific annealing to complementary sequences in ligation products and amplification products, as appropriate.

According to certain embodiments, primer sets according to the present invention comprise at least one first primer and at least one second primer. In certain embodiments, the first primer of a primer set is designed to hybridize with the complement of the 5' primer-specific portion of a target sequence or an amplification product in a sequence-specific manner. In certain embodiments, the second primer in that primer set is designed to hybridize with a 3' primer-specific portion of the same target sequence or amplification product in a sequence-specific manner.

"Target polynucleotide" according to the invention comprises a polynucleotide as defined above. The term "target polynucleotide" according to the present invention more specifically comprises a specific nucleic acid sequence, the presence or absence or sequence of which is to be detected. The person of ordinary skill will appreciate that while the target polynucleotide is typically described as a single-stranded molecule, the opposing strand of a double-stranded molecule comprises a complementary sequence that may also be used as a target.

The target polynucleotide may be derived from any biological source, including, but not limited to, viruses, prokaryotes, protists, eukaryotes, plants, fungi, and animals. Samples of these sources may include, but are not limited to, whole blood, a tissue biopsy, bone marrow, semen, sputum, urine, amniotic fluid, sperm, hair, skin, and cultured cells. In certain embodiments, presence of the target polynucleotide may be used to indicate the presence of a pathogen, a specific allele, a genetic disease, predisposition to a genetic disease, cell surface antigens, serotype, HLA type, TAP1, TAP2, or MICA.

An "indicator molecule" is any molecule which can be used to determine the presence of amplification product during or after an amplification reaction. The skilled artisan will appreciate that many indicator molecules may be used in the present invention. For example, according to certain embodiments, indicator molecules include, but are not limited to, fluorophores, radioisotopes, chromogens, enzymes, antigens, heavy metals, dyes, magnetic probes, phosphorescence groups, chemiluminescent groups, and electrochemical detection moieties.

A "fluorescent indicator" is any molecule or group of molecules designed to indicate the amount of amplification product by a fluorescent signal. In certain embodiments, such fluorescent indicators are "nucleic acid binding molecules" that bind or interact, e.g., through ionic bonds, hydrophobic interactions, or covalent interactions with nucleic acid. Complex formation with the minor groove of double stranded DNA, nucleic acid hybridization, and intercalation are all non-limiting examples of nucleic acid binding for the purposes of this invention. In certain embodiments, such fluorescent indicators are molecules that interact with double stranded nucleic acid. In certain embodiments, fluorescent indicators may be "intercalating fluorescent dyes," which are molecules which exhibit enhanced fluorescence when they intercalate with double stranded nucleic acid. In certain embodiments, "minor groove binding fluorescent dyes" may bind to the minor groove of double stranded DNA. In certain embodiments, fluorescent dyes and other fluorescent molecules can be excited to fluoresce by specific wavelengths of light, and then fluoresce in another wavelength. According to certain embodiments, dyes may include, but are not limited to, acridine orange; ethidium bromide; thiazole orange; pico green; chromomycin A3; SYBR® Green I (see U.S. Pat. No. 5,436,134); quinolinium, 4-[(3-methyl-2(3H)-benzoxazolylidene) methyl]-1-[3-(trimethylammonio) propyl]-, diiodide (YO-PRO®); and quinolinium, 4-[(3-methyl-2(3H)-benzothiazolylidene) methyl]-1-[3-(trimethylammonio) propyl]-, diiodide (TOPRO®). SYBR® Green I, YOPRO®, and TOPRO® are available from Molecular Probes, Inc., Eugene, Oreg.

According to certain embodiments, the fluorescent indicators may be "5'-nuclease fluorescent indicators," which are fluorescent molecules attached to fluorescence quenching molecules by a short oligonucleotide. According to certain embodiments, the fluorescent indicator binds to the target molecule, but is broken by the 5' nuclease activity of the DNA polymerase when it is replaced by the newly polymerized strand during PCR, or some other strand displacement protocol. When the oligonucleotide portion is broken, the fluorescent molecule is no longer quenched by the quenching molecule, and emits a fluorescent signal. An example of such a 5'-nuclease fluorescent indicator system has been described in U.S. Pat. No. 5,538,848, and is exemplified by the TaqMan™ molecule, which is part of the TaqMan™ assay system (available from Applied Biosystems).

According to certain embodiments, the fluorescent indicators may be "molecular beacons," which comprise a fluorescent molecule attached to a fluorescence-quenching molecules by an oligonucleotide. When bound to a polynucleotide as double stranded nucleic acid, the quenching molecule is spaced apart from the fluorescent molecule, and the fluorescent indicator may give a fluorescent signal.

When the molecular beacon is single stranded, the oligonucleotide portion can bend flexibly, and the fluorescence-quenching molecule can quench the fluorescent molecule, reducing the amount of fluorescent signal. Such systems are described in U.S. Pat. No. 5,723,591.

"Amplification product" refers to nucleic acid products resulting from an amplification reaction.

"Reaction composition" refers to a composition used to amplify target polynucleotides. In certain embodiments, the reaction composition comprises amplification primers specific to a target polynucleotide. In certain embodiments, the reaction composition comprises amplification primers specific to a target polynucleotide and a fluorescent indicator. In certain embodiments, the reaction composition may also include, but is not limited to, enzymes, salts, reagents, and buffers used in an amplification reaction.

The term "sequencing primer" refers to an oligonucleotide primer which is used to initiate a sequencing reaction performed on a nucleic acid.

EXEMPLARY EMBODIMENTS

According to certain embodiments, the invention includes methods and kits that monitor the progress of nucleic acid amplification. In certain embodiments, the methods and kits can be used for genotyping and clinical diagnoses. The current invention eliminates a need to analyze amplification products by gel electrophoresis. According to certain embodiments, the invention will facilitate high throughput screening of genotyping samples by saving labor and time. Moreover, according to certain embodiments, the invention reduces subjective analysis of a human technician, which can be a source of error in the analysis.

Any type of amplification can be used for various embodiments of the invention. Exemplary amplification methods include, but are not limited to, PCR, the ligase chain reaction (LCR), Q-beta replicase-based systems, NASBA, 3SR, and rolling circle replication. In certain embodiments, PCR is the amplification method used.

Methods of optimizing amplification reactions are well known to those skilled in the art. For example, it is well known that PCR may be optimized by altering times and temperatures for annealing, polymerization, and denaturing, as well as changing the buffers, salts, and other reagents in the reaction composition. Optimization can also be affected by the design of the amplification primers used. For example, the length of the primers, as well as the G-C:A-T ratio can alter the efficiency of primer annealing, thus altering the amplification reaction. See James G. Wetmur, "Nucleic Acid Hybrids, Formation and Structure," in Molecular Biology and Biotechnology, pp.605-8, (Robert A. Meyers ed., 1995).

During amplification, an indicator molecule is included in the amplification reaction. According to certain embodiments, this molecule indicates the amount of double-stranded DNA in the reaction, and thus serves as a measure of the amount of amplification product produced. In certain embodiments, the indicator molecule is a fluorescent indicator. In certain embodiments, the fluorescent indicator is a nucleic acid binding molecule which binds with the DNA, resulting in a change in its fluorescent qualities. Exemplary dyes of this type include, but are not limited to, acridine orange, ethidium bromide, and SYBR® Green I (Molecular Probes, Inc.) (see U.S. Pat. No. 5,436,134).

In certain embodiments, the fluorescent indicator can be a fluorescing dye connected to a quenching molecule by a specific oligonucleotide. These include, but are not limited to, 5'-nuclease fluorescent indicators and molecular beacons. Examples of such systems are described, e.g., in U.S. Pat. Nos. 5,538,848 and 5,723,591.

In certain embodiments, the amount of fluorescent indicator that gives a fluorescent signal in response to an emitted light typically relates to the amount of double stranded nucleic acid produced in the amplification reaction. Thus, the amount of fluorescent signal is typically related to the amount of double stranded product created in the amplification reaction. In such embodiments, one can therefore measure the amount of amplification product by measuring the intensity of the fluorescent signal from the fluorescent indicator. According to certain embodiments, one can employ an internal standard to quantify the amplification product indicated by the fluorescent signal.

Devices have been developed that can perform a thermal cycling reaction with compositions containing a fluorescent indicator, emit a light beam of a specified wavelength, read the intensity of the fluorescent dye, and display the amount of amplification product after each cycle. Devices comprising a thermal cycler, light beam emitter, and a fluorescent signal detector, such as the ABI Prism® 5700, are available from Applied Biosystems, and have been described in U.S. Pat. Nos. 5,928,907; 6,015,674; and 6,174,670.

In certain embodiments, each of these functions may be performed by separate devices. For example, if one employs a Q-beta replicase reaction for amplification, the reaction may not take place in a thermal cycler, but could include a light beam emitted at a specific wavelength, detection of the fluorescent signal, and calculation and display of the amount of amplification product.

In certain embodiments, combined thermal cycling and fluorescence detecting devices can be used for precise quantification of target polynucleotides in samples. In certain embodiments, fluorescent signals can be detected and displayed during or after each thermal cycle, thus permitting monitoring of amplification products as the reactions occur in "real time." In certain embodiments, one can use the amount of amplification product and number of amplification cycles to calculate how much of the target polynucleotide was in the sample prior to amplification.

According to certain embodiments, one could simply monitor the amount of amplification product after a predetermined number of cycles sufficient to indicate the presence of the target polynucleotide in the sample. One skilled in the art can easily determine, for any given sample type, primer sequence, and reaction condition, how many cycles are sufficient to determine the presence of a given target polynucleotide.

According to certain embodiments, the amplification products can be scored as positive or negative as soon as a given number of cycles is complete. There is no need to analyze the products by gel electrophoresis, since the fluorescent signal will indicate whether or not target polynucleotides have been amplified to provide amplification product. In certain embodiments, the results may be an endpoint in the analysis, or they may be used to determine which reaction products can be subjected to further analysis. In certain embodiments, the results may also be transmitted electronically directly to a database and tabulated. Thus, in certain embodiments, large numbers of samples may be processed and analyzed with less time and labor required.

In certain embodiments, the results of the amplification reaction are used to determine which of the amplification products to subject to sequencing reactions. In certain embodiments, the sequencing reactions are then read by a sequencing apparatus to determine the sequence. According to certain embodiments, the sequencing apparatus is automatic.

In certain embodiments, one sequences the amplification product that is produced from the reaction composition that includes the fluorescent indicator.

In certain embodiments, one does not actually sequence the amplification product from the reaction composition that includes the fluorescent indicator. In certain such embodiments, one uses at least one set of reaction compositions. The at least one set comprises a first reaction composition and a second reaction composition, which both comprise primers specific for the same target polynucleotide. Nucleic acid from the sample is combined with each set of reaction compositions. The reaction compositions are subjected to the same amplification reaction. The first reaction composition, which further comprises a fluorescent indicator, is used to determine if amplification product is present in both the first and second reaction compositions. If amplification product is present, amplification product from the second reaction composition is sequenced.

According to certain embodiments, different fluorescent indicators may distinguish between different target polynucleotides. A non-limiting example of such an indicator is a 5'-nuclease fluorescent indicator, such as the TaqMan™ molecule, wherein a fluorescent molecule is attached to a fluorescence-quenching molecule by an oligonucleotide. The oligonucleotide portion of the fluorescent indicator may bind to a specific target polynucleotide. Different 5'-nuclease fluorescent indicators, each fluorescing at different wavelengths, can distinguish between different amplification products within the same amplification reaction. In certain embodiments, this method could be employed to determine which sequencing primers are to be used for sequencing the amplification product.

For example, one could use three different 5'-nuclease fluorescent indicator molecules that fluoresce at three different wavelengths and that are specific to three different target polynucleotides. After amplification, one can determine which specific target polynucleotides are present based on the wavelength of signal detected. That information can then be used in selecting specific sequencing primers to be used in a subsequent sequencing reaction. Thus, if only wavelength A is detected, one would know to use sequencing primers specific for the target polynucleotide associated with the specific 5'-nuclease fluorescent indicator molecule that fluoresces at wavelength A.

In certain embodiments, other methods of distinguishing between two different target sequences can be employed. In certain embodiments, two oligonucleotide probes which distinguish between sequences may be differentially cleaved, depending on the target polynucleotide present, to emit a fluorescent signal related to the amount of each target polynucleotide present. Such systems are described, e.g., in U.S. Pat. Nos. 5,846,717; 5,985,557; 5,994,069; and 6,001,567; and exemplified by the Invader® Assay System, Third Wave Technologies, Inc.

In certain embodiments, the primers used in the amplification reaction are used to distinguish between groups of allele types, such as those within HLA class molecules, as a non-limiting example. For instance, in certain HLA-DRB typing embodiments, alleles can be divided into allele groups including, but not limited to, DRB1, DRB3, DRB4, and DRB5. Different amplification primers specific to each of these groups can be used to produce amplification products for alleles classified within each of these groups. In certain embodiments, first, one determines which groups are present by determining which amplification reactions contain amplification product. Then, those positively amplified products are sequenced to determine specifically which HLA-DRB alleles are present within each allele group in the sample. Several primers specific to alleles within HLA classes I and II have been described previously, e.g., in U.S. Pat. No. 6,103,465. Commercially available products that include primers for HLA typing and other components for PCR amplification include the HLA-A, HLA-B, and HLA-DRB Sequencing-Based Typing Starter Kits, and HLA-DRB Reagent Kit with BigDye™ Terminators (available from Applied Biosystems).

In certain embodiments, the amplification reactions may be used to distinguish between different classes, species, or strains of pathogens, such as infectious bacteria. After identifying the different class by a positive signal, the amplification product can be sequenced to further define what variety of pathogen is present in the sample.

Further, in certain embodiments, kits are provided which include amplification primers for analysis of polymorphic alleles, fluorescent indicators that can detect amplification products, and sequencing primers that can be used in sequencing reactions. In certain embodiments, the kits include sequence terminators for sequencing the reaction products. In certain embodiments, the kits may contain primers for analysis in distinguishing between a variety of different pathogens. In certain embodiments, the kits may contain primers for distinguishing between different allelic genotypes. In certain embodiments, the sequence terminators are fluorescently labeled. In certain embodiments, the sequencing primers are fluorescently labeled.

The following example of HLA-DRB typing illustrates certain embodiments of the invention, and does not limit the scope of the invention in any way.

EXAMPLE 1

Low Resolution HLA-DRB Typing

Genomic DNA was purified using Qiagen's protocol "Isolation of Genomic DNA from Buccal Swabs" and Qiagen's DNeasy™ Kit (Cat. No. 69504, Qiagen, Inc.). After isolation, 40 µl of genomic DNA from human buccal swabs was added to 1 µl of AmpliTaq Gold® DNA Polymerase (Roche Molecular Systems, Inc.). To each well of an ABI Prism® 5700 Optical Plate, 2.5 µl of the DNA-enzyme mixture was added. Then, 10 µl of different HLA mix was added from Applied Biosystems HLA-DRB BigDye™ Terminator, Sequencing-Based Typing Kit (Part No. 4305026), to each well. Each HLA mix contained a different primer set, designed to amplify different allele groups of HLA-DRB. Also, 12.5 µl SYBR® Green PCR Master Mix (Part No. 4309155), was added to each well. The plate was then covered with an ABI Prism Optical Plate Adhesive Cover (Part No. 4311971).

The parameters for thermal cycling were as follows:
95° 10 minutes
96° 20 seconds
65° 30 seconds
72° 30 seconds The last three steps were repeated for 36 cycles. Thermal cycling was conducted on an ABI Prism® 5700 Sequence Detection System, using the operating protocols provided with the system. This apparatus was also used to calculate the dissociation curve of the amplified product using the operating protocols provided with the system. That dissociation curve was used to calculate the relative purity of the product.

The results of the low resolution typing are shown in FIGS. 1 and 2. Low resolution typing shows which HLA-DRB allele groups are present in a sample, but not which specific alleles are present within an allele group. FIG. 1 shows a comparison of the results as analyzed by the ABI Prism® 5700, and standard electrophoresis on an agarose gel. Amplified product analyzed using the ABI Prism® 5700 could directly be used in sequencing reactions, while the amplified product subjected to electrophoresis could not be further analyzed without an additional purification step.

High Resolution HLA-DRB Typing

After determining which amplification reactions above contained positive amplification products, 2 µl of PCR product was added to 6 µl diluent from Applied Biosystems HLA-DRB BigDye™ Terminator, Sequencing-Based Typing Kit (Part No. 4305026). The diluted PCR product was then subjected to a sequencing reaction as follows. Eight µl of the forward sequencing mix from Applied Biosystems HLA-DRB BigDye™ Terminator, Sequencing-Based Typing Kit (Part No. 4305026), was added to 2 µl of the diluted positive PCR product. Separately, 8 µl of the reverse sequencing mix from Applied Biosystems HLA-DRB BigDye™ Terminator, Sequencing-Based Typing Kit (Part No. 4305026), was added to 2 µl of the diluted positive PCR product.

The parameters for the cycle sequencing reactions were as follows:
96° 10 seconds
96° 10 seconds
50° 10 seconds
60° 2 minutes The last three steps were repeated for 20 cycles, then followed by a hold step at 4° C. Samples were then purified by a Centri-Sep™ spin column (Cat. No. CS-900, Princeton Separations, Inc.) and run on a ABI Prism® 3100 Genetic Analyzer using the protocol provided with that product.

A sample of the total results of the high resolution typing are shown in FIG. 3. High resolution HLA-DRB typing shows not only which HLA-DRB allele groups are present in a sample, but also shows specific alleles within those groups. The sequenced reaction product that was subjected to the low resolution HLA-DRB typing, containing SYBR® Green I, was compared to a sequencing reaction product of the same sample and amplification product containing no SYBR® Green I. The results show no detectable adverse effect on the sequencing reaction by the fluorescent indicator.

FIG. 4 shows the sequenced sample data analyzed by the Applied Biosystems MatchTools™ software to get a Preliminary Report, which shows which HLA-DRB allele groups were present in the sample. The data was then edited in Applied Biosystems MT Navigator software, which analyzed the nucleotide sequence data from the ABI Prism® 3100 Genetic Analyzer, before being resubmitted to the Applied Biosystems MatchTools™ software for a Final Report (FIG. 4). MatchTools™ and MT Navigator™ software are both available as accessories with the Applied Biosystems Starter HLA-DRB Sequencing Based Typing Kit (Part No. 4305026). The Final Report shows that this sample was an exact match to HLA-DRB alleles 11011, 11011/1105, and 1105. Thus, the precise HLA-DRB alleles in the sample were HLA-DRB11011 and HLA-DRB1105.

What is claimed is:

1. A method of determining the presence and sequence of at least one target polynucleotide in a sample comprising:

combining nucleic acid from the sample with at least one set of reaction compositions comprising a first reaction composition and second reaction composition, both specific for the at least one target polynucleotide, wherein the first reaction composition comprises amplification primers specific to the at least one target polynucleotide and lacks a fluorescent indicator, and the second reaction composition comprises a fluorescent indicator and amplification primers specific to the at least one target polynucleotide, and wherein the first reaction composition and the second reaction composition are separate reaction compositions;

amplifying the at least one target polynucleotide present in the reaction compositions using the amplification primers to obtain at least one amplification product;

irradiating the at least one amplification product of the second reaction composition such that the fluorescent indicator produces a fluorescent signal, wherein the intensity of the fluorescent signal is related to the quantity of the at least one amplification product;

monitoring the amplifying of the second reaction composition by detecting the fluorescent signal from the fluorescent indicator;

determining whether the at least one amplification product is present in both the first reaction composition and the second reaction composition from the intensity of signal from the fluorescent indicator in the second reaction composition; and determining the sequence of the at least one amplification product of the first reaction composition if the at least one amplification product is present in the first reaction composition.

2. The method of claim 1, wherein the determining of the sequence comprises:

performing a sequencing reaction on the at least one amplification product to obtain a sequencing product; and placing the product of the sequencing reaction into a sequencing apparatus to determine a sequence of the at least one amplification product.

3. The method of claim 2, wherein the fluorescent signal is detected using a device.

4. The method of claim 3, wherein the amplifying, irradiating, and monitoring comprise use of a thermal cycler, a device that irradiates the at least one amplification product, a device that detects resulting fluorescence during each cycle, and a device that displays the increase in fluorescence by cycle number.

5. The method of claim 4, wherein the thermal cycler, the device that irradiates, the device that detects, and the device that displays are all components of a single device.

6. The method of claim 3, wherein nucleic acid from the sample is combined with at least two different sets of separate reaction compositions comprising the first reaction composition and the second reaction composition, wherein each set of separate reaction compositions comprises amplification primers specific for a different target polynucleotide, and wherein the amplifying results in different amplification products if the different target polynucleotides are present in the sample.

7. The method of claim 4, wherein the amount of amplification product and number of cycles are used to determine the amount of target polynucleotide present in the sample prior to the amplification.

8. The method of claim 3, wherein the monitoring occurs after the amplifying is complete.

9. The method of claim 4, wherein the monitoring occurs during two or more cycles during the amplifying.

10. The method of claim 3, wherein the nucleic acid from the sample is derived from at least one biological source selected from a virus, a prokaryote, a protist, a plant, a fungus, and an animal.

11. The method of claim 3, wherein the presence of a given target polynucleotide indicates the presence of a pathogen, wherein the pathogen is at least one pathogen selected from a virus, a prokaryote, and a eukaryote.

12. The method of claim 11, wherein the pathogen is at least one pathogen selected from HIV, specific *E. coli* strains, *Salmonella* species, and *Haemophllus* species.

13. The method of claim 3, wherein the presence of a given target polynucleotide indicates the presence of at least one of a genetic disease and/or a genetic predisposition to a disease.

14. The method of claim 3, wherein the presence of a given target polynucleotide indicates the presence of a specific allele.

15. The method of claim 14, wherein the presence of the specific allele indicates serotype.

16. The method of claim 14, wherein the presence of one or more specific alleles indicates one or more cell surface proteins which determine at least one HLA type.

17. The method of claim 16, wherein the at least one HLA type comprises at least one HLA type selected from HLA-A, HLA-B, HLA-C, HLA-E, HLA-F, HLA-G, HLA.DRA, HLA-DRI1, HLA-DRB2, HLA-DRB3, HLA-DRB4, HLA-DRB5, HLA-DQA1, HLA-DQB1, HLA-DPA1, HLA-DPB1, HLA-DOA, HLA-DOB, HLA-DMA, and HLA-DMB.

18. The method of claim 3, wherein the presence of a given target polynucleotide indicates the presence of at least one polynucleotide selected from TAP1, TAP2, and MICA.

19. The method of claim 3, wherein the fluorescent indicator is a nucleic acid binding molecule.

20. The method of claim 19, wherein the fluorescent indicator is an intercalating dye.

21. The method of claim 19, wherein the fluorescent indicator is a minor groove binding molecule.

22. The method of claim 19, wherein the fluorescent indicator is a molecular beacon.

23. The method of claim 3, wherein the fluorescent indicator is at least one fluorescent indicator selected from unsymmetric cyanine dye; thiazole orange; ethidium bromide; pico green; acridine orange; quinolinium 4-[(3-methyl-2(3H)-benzoxazolylidene) methyl]-1-[3-(trimethylammonio) propyl]-diiodide; quinolinium 4-[(3-methyl-2(3H)-benzothiazolylidene) methyl]-1-[3-(trimethylammonio) propyl]-diiodide; and chromomycin A3.

24. The method of claim 3, wherein the fluorescent indicator is a 5'-nuclease fluorescent indicator.

25. The method of claim 3, wherein the sample is at least one sample selected from whole blood, a tissue biopsy, bone marrow, semen, sputum, urine, amniotic fluid, sperm, hair, skin, and cultured cells.

* * * * *